(12) United States Patent
Stano

(10) Patent No.: US 8,007,456 B2
(45) Date of Patent: Aug. 30, 2011

(54) VARIOUSLY ADJUSTABLE NIGHT SPLINT WITH ADJUSTABLE SPACERS AND LOCK-OUT HINGE

(76) Inventor: William S. Stano, Boise, ID (US)

( * ) Notice: Subject to any disclaimer, the term of this patent is extended or adjusted under 35 U.S.C. 154(b) by 585 days.

(21) Appl. No.: 11/262,650

(22) Filed: Oct. 28, 2005

(65) Prior Publication Data

US 2006/0064048 A1 Mar. 23, 2006

Related U.S. Application Data

(63) Continuation-in-part of application No. 10/641,886, filed on Aug. 14, 2003, now abandoned.

(51) Int. Cl.
*A61F 5/00* (2006.01)
*A61F 5/37* (2006.01)

(52) U.S. Cl. ............... 602/27; 602/16; 602/28; 128/882

(58) Field of Classification Search ............ 602/12, 602/23, 27, 16, 28, 29; 128/882
See application file for complete search history.

(56) References Cited

U.S. PATENT DOCUMENTS

| | | | |
|---|---|---|---|
| 1,575,042 A | 1/1925 | Denniston | |
| 4,289,122 A * | 9/1981 | Mason et al. | 602/27 |
| 4,369,588 A | 1/1983 | Berguer | |
| 5,088,479 A * | 2/1992 | Detoro | 602/27 |
| 5,224,925 A | 7/1993 | Varn | |
| 5,328,444 A * | 7/1994 | Whiteside | 602/16 |
| 5,486,157 A | 1/1996 | DiBenedetto | |
| 5,609,570 A | 3/1997 | Lamont | |
| 5,700,237 A | 12/1997 | Hess | |
| D395,514 S | 6/1998 | Stano | |
| 5,776,090 A | 7/1998 | Bergmann et al. | |
| 5,799,659 A * | 9/1998 | Stano | 128/882 |
| 6,171,272 B1 | 1/2001 | Akita et al. | |
| 6,267,742 B1 | 7/2001 | Krivosha et al. | |
| 2003/0153859 A1* | 8/2003 | Hinshon | 602/27 |

* cited by examiner

*Primary Examiner* — Michael Brown
*Assistant Examiner* — Keri J Nelson
(74) *Attorney, Agent, or Firm* — Dykas & Shaver, LLP

(57) ABSTRACT

A low cost foldable orthosis for the treatment of foot and ankle conditions including plantar facitis and tendonitis, the orthosis is a foldable molded portion manufactured in a variety of incremental sizes, having a generally U-shaped cross-sectional configuration and a flat foot bed, interconnected by a hinge. This device includes a variety of spacers which enable the angle of covered by a soft fabric covering, and using a removable and interchangeable foot bed wedge insert permitting the angle of dorsiflexion, plantar flexion, inversion and eversion to be varied.

18 Claims, 14 Drawing Sheets

VARIOUSLY ADJUSTABLE NIGHT SPLINT WITH ADJUSTABLE SPACERS AND LOCK-OUT HINGE

CLAIM TO PRIORITY

This application is a continuation-in-part application which claims the priority date from the application entitled FOLDABLE ORTHOSIS NIGHT SPLINT WITH ORTHOWEDGE filed by William S. Stano on Aug. 14, 2003 with application Ser. No. 10/641,886, now abandoned, the disclosure of which is incorporated herein by reference.

BACKGROUND OF THE INVENTION

1. Field of the Invention

The present invention relates to orthotic medical devices and more specifically to a foldable adjustable night splint which can be used for treating and facilitating the treatment of a variety of conditions including pain in the foot and heel caused by contracture of the plantar fascia and/or the Achilles tendon, treatment of hip ailments, and post-surgery treatment of the foot.

2. Background

Simply put, the human foot takes the brunt of the impact of every step experienced by an individual. It is also likely that the single largest source of complaint for foot ailments is related to heel pain. One source of heel pain commonly observed is due to a condition known as recalcitrant plantar facitis. Plantar facitis occurs in the plantar fascia, a fibrous membrane disposed longitudinally across the bottom of the foot. The plantar fascia is attached at the heel bone, more specifically to the inner tubercle of the os calcis. The plantar fascia becomes broader and thinner as it extends longitudinally across the bottom of the foot, eventually dividing near the heads of the metatarsal bones into five processes, one for each of the five toes.

The strongest ligament in the body is the plantar fascia, a fibrous band of tissue that starts on the bottom surface of the heel bone and extends forward on the bottom of the foot to just behind the toes. Its function is to protect the softer muscles and tissues of the bottom of the foot from injury, as well as to help maintain the integrity of the foot structure itself. If the fascia becomes stretched or strained, the arch area, as well as about the heel bone, become tender and swollen. This inflammation is called plantar facitis and is painful from the heel throughout the arch up into the Achilles tendon. These patients usually have tight and inflexible heel cords, a condition that is referred to as Achilles tendon tightness.

When the heel cord is tight, it causes compensation in the foot with over-pronation of the foot during weight bearing. The pain is consistently worse when you first get up in the morning and at the end of the day. The pain usually lurks in the heel pad and may include the arch ligament. The natural tendency is to ignore the symptoms of the pain at first.

Heel pain like plantar facitis is often times caused by contracture of the Achilles tendon and the plantar fascia, which can occur at night during sleep or during daytime inactivity. The Achilles tendon is the strongest and thickest tendon in the human body. The Achilles tendon begins at or about the middle of the posterior side of the leg extending downward towards the heel, narrowing as it progresses towards its point of insertion at the posterior surface of the os calcis. When an individual is standing, walking, running or even sitting in a position in which the feet are in contact with the floor or other surface, both the plantar facia and the Achilles tendon are extended to varying degrees depending of course on the nature and intensity of the activity. During sleep, an individual has a natural tendency to plantar-flex the ankle joint beyond the position which is normal during walking, standing or sitting with one's feet on the floor. Plantar flexion is when the bottom of the foot is extended so as to form an angle with the lower leg of greater than 90°. Dorsiflexion is the opposite motion; when the foot is moved to a position in which the bottom of the foot forms an angle with the lower leg of less than 90°, this is dorsiflexion.

As a result of plantar flexion during the night, the plantar facia and the Achilles tendon contract from their size and dimension normal to the walking, standing or sitting positions. Upon arising, the plantar facia and the Achilles tendon are once again extended and stretched when the feet and ankles resume a normal position associated with walking or standing. Typically, it is when an individual arises following sleep or a period of extended recumbency that the effects of heel pain associated with plantar facitis, with or without the associated Achilles tendon contracture, are observed. In a significant number of cases, the pain has been described as substantial.

Various theories explain the constant pull of the plantar fascia at the insertion of the heel bone. The plantar fascia and intrinsic muscles can cause spurs or tearing of the fascia at the insertion. With continued pull, subperiosteal bleeding can produce calcification leading to new bone. Other theories are constant stress of the fascia with excessive stress at the insertion forming new connective tissue with the tissue going from fibrocartilaginous tissue to cartilaginous to bone. A reference to the thickening of the plantar ligaments is found as early as 1859 in a dissection of a flat foot by Dr. Wood.

In various types of occupations, sedentary work may produce atrophy and degeneration of the shock absorption ability of the heel's fat pad. Occupations which produce over use of tissue, which is stressed beyond its physiologic limits, such as working at a factory machine or the static loading exposure of welding, may also cause fat pad atrophy and degeneration from long, unnatural hours of standing on hard surfaces owing to the degeneration of the plantar fascia.

Plantar facitis is a condition characterized by tenderness located at or near the point at which the plantar fascia attaches to the heel bone, or the os calcis. This condition has been traditionally treated in a number of ways, including non-steroidal anti-inflammatory medicines, cortisone injections, shoe modifications, physical therapy, and even surgery.

Plantar facitis is referred to in a book written by Dr. Scholl in 1915, as "policeman's heel." Reference can be found in literature on heel pain before 1900. Authors writing about the conditions affecting the foot referenced it as pain of various courses from systemic disease to pain related to the plantar fascia. In 1860, Zacharie discussed a condition affecting the heel in which patients had greater pain in the morning than after standing and walking for one or two hours. In 1900, Plettner noticed inferior heel spurs on patients' radiographs. After that, many theories were put forth on the cause of heel pain and plantar facitis and the amount of references in the literature had more prevalence in this time. In 1915, Dr. Scholl indicated that a flat foot usually accompanied painful heel pain, giving us the revelation that there was a correlation between pronation and painful heels.

The earliest records reviewed which found treatment for heel pain, was in a 1915 article by Waechter and Sonnenschein in which they used felt aperture pads for the treatment of painful heel pain. Dr. Scholl in 1915 advocated the use of a metal orthotic called the Trispring. Metal was placed into the arch to support it and prevent elongation of the arch and a leather top was applied over the metal. Dr. Carl Bergman, in his orthopedic lecture notes taken at the Illinois College of Chiropody in 1919, suggests the use of a sponge heel pad in the shoe for the local relief of heel pain.

Favorable results for the treatment of plantar facitis have been observed in a study that employed night splints in connection with other non-surgical therapeutic measures to treat this condition. See Wapner and Sharkey, "The Use Of Night Splints For Treatment Of Recalcitrant Plantar Facitis," *Foot and Ankle* Vol. 12, No. 3, December 1991. The night splint consists, essentially, of a boot-like structure that is strapped to a patient's lower leg and foot, holding the foot relative to the lower leg in a position such that the ankle joint is held in slight dorsiflexion. In so doing, both the plantar fascia and the Achilles tendon are slightly extended and are not allowed to contract during the night. The use of night splints, together with the variety of other elements of treatment including anti-inflammatory medications, physical therapy, and foot cushions for use during the daytime, has proved beneficial in the treatment of plantar facitis.

It is desirable to have an orthosis that has the possibility of inducing inversion or eversion of a patient's foot. Inversion is when the bottom of the foot, the plantar surface, faces more toward the midline of the body. Eversion is motion of the foot in which the plantar surface of the foot is tilted so as to face further away from the midline of the body.

One method of treating such conditions is through the use of splints. An example of the types of splints that are used to treat these conditions are custom molded ankle-foot orthosis constructed of polypropylene which were described in a study by Wapner/Sharkey as costing each patient approximately $200.00.

It is suggested that the relatively high price of the splints used in the Wapner-Sharkey study is due in part to the requirement that custom molding is required to form the splint to conform to the patient's anatomy. This individualized process then also requires that a custom molded orthosis can be used by only one patient. Various other splints are advertised for treatment of plantar facitis that also typically consist of a molded splint or a combination of molded plastic and metal framework, with the dorsiflexion set at 5°.

Although similar in appearance to foot and ankle casts, also called walking casts, a night splint for the treatment of plantar facitis is only superficially similar to a walking cast. A foot or ankle cast is made so that the force vector of the patient's weight passes vertically through the cast and the patient's leg when he/she is standing. In the medical industry, no walking casts are made that do not place the bottom of the patient's foot at a 90° angle to the patient's leg, which is consistent with a vertical force vector. Thus, no walking casts are built to induce and maintain dorsiflexion or plantar flexion. In addition, a walking cast is made to provide the patient with a weight-bearing region forward of the heel, on which the weight of the body is placed when walking, and from which the patient can pivot forward when taking the next stride. The bearing and pivoting structure can be a rounded knob under the mid region of the foot, or it can be a rounded surface which covers the bottom of the cast from heel to toe. A walking cast may also have a cushioning region directly under the heel to absorb some of the shock of walking.

Walking casts are not made to wear in bed at night, and are not made to induce a stretching effect on tendons. They are made to provide support to healing ankle and foot joints and bones, and to control the motion of these healing joints and bones while healing takes place.

To treat plantar facitis, it is necessary to use considerable force to counteract the strong muscles and tendons of the lower leg and foot. If this force is applied improperly, pressure points can result, thus causing discomfort and complications for some patients.

Some patients have reduced blood circulation or sensation in the feet, such as patients with diabetes, vascular insufficiency, polio, stroke, trauma, or neurological problems. In such patients, if they need to use a night splint for treatment of plantar facitis, it is important to minimize the pressure points exerted by the night splint on the patient's foot, while still exerting the necessary force on the foot and lower leg structure. The night splint must also not bruise or scratch the collateral leg during sleep, must not soil or tear bedding, and must be compatible with a sleeping partner. Walking casts are not designed to accomplish these objects.

Another ailment for which a night splint is needed is calcaneal apophysitis. This is typically of a problem which presents in juveniles. It is basically a case of the bones of the leg and foot growing faster than the connective tissue, such as the plantar fascia and Achilles tendon, and the heel bone is immature and somewhat soft. These two tendons are put under strain and cause heel pain. Treatment of calcaneal apophysitis has proven to be very successful using a night splint. The night splint prevents foot drop during sleep, and helps lengthen the two involved tendons.

Paratendon tendonitis is another condition for which a night splint is needed for successful treatment. The paratendon is a thin sheath-like covering of tendons. The lining of this structure can become inflamed, and require nighttime stabilization to immobilize the foot and lower leg, and treatment.

Achilles tendonitis is another condition for which a night splint is needed for successful treatment. Achilles tendonitis can result from overuse of the tendon in sports activities, and can also result from a number of inflammatory diseases, of which rheumatoid arthritis is one. Use of a night splint is an effective treatment for this ailment, since immobilizing the Achilles tendon without allowing night drop or contracture of the tendon is the best treatment.

Another area where a night splint is needed is after various surgeries on the hip. After hip replacement, for instance, it is desired that the involved hip joint remain absolutely immobile. What is needed is a device that immobilizes one or both feet and lower legs, so that the hip joint is not moved.

Another situation that requires the use of a night splint is when surgery has been performed on tendons in the foot. If the tendons worked on are on the medial side of the foot, it is desirable for the foot to be held in an inverted position (with the plantar surface facing toward the midline of the body), which relieves strain on the affected tendons. If the tendons worked on are on the lateral side of the foot, an everted position is desirable.

Night splints function best when they can be used on a continuous ongoing basis, thus allowing the tendons to be appropriately stretched into a desired position. One problem that exists with walking casts and similar devices is that they are bulky and are difficult to store in a desired position. Another problem is that such devices have an upper portion and a lower portion that is configured in relatively fixed positions relative to one another. This results in many of the devices shown in the prior art being large and bulky and not easily stored for transport or storage. As a result of this phenomenon, many times the individuals who should utilize such devices, fail to do so. In addition, this fixed configuration limits the flexibility and functionality of the device in treating various conditions where the desired positioning of the foot and the lower leg are different from the positioning which is available in the fixed configuration.

Accordingly, it is an object of the invention to provide a flexible selectively adjustable orthosis which is suitable for use on a patient's foot and lower leg during the night, as a night splint for the treatment of plantar facitis, Achilles tendon problems, hip immobilization, post-surgery treatment of the foot, and other conditions.

Additional objects, advantages and novel features of the invention will be set forth in part in the description which follows and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

The present invention is a foldable, selectively adjustable night splint which can be utilized to treat a variety of conditions related to the foot and lower leg. The device of the present invention is made up of a foldable shell that includes an upper portion and a lower portion. Both portions are generally U-shaped in cross-section. The lower section has a generally flat foot bed portion. The upper and lower sections are pivotally connected one to one another so that the upper and lower sections are foldable from a first position wherein the lower section extends from the generally upright upper portion at an angle of about 90° to a second position wherein the upper portion is generally folded over upon the lower foot bed section of the device. The upper and lower sections are structurally configured to be locked or maintained in a desired position of about 90° by the structure of the upper and lower sections themselves. The present invention also includes a plurality of spacer pieces which are utilized to fit between the upper and lower portions of the device so as to vary the degree and angle at which the upper portion and the lower portion are positioned.

The upper section is configured to generally conform to the lower portion of the human leg, and the lower section is configured to receive a bottom surface of a foot attached to a human leg. A removable wedge foot bed insert may be included as part of the device and it is configured to be received in the foot bed portion of the lower portion. The wedge is typically inclined from a heel portion to a toe portion and thus forms an inclined foot bed that prevents plantar flexion and promotes dorsiflexion. A securing mechanism is also included as part of the device and is used to secure a patient's foot in the device for treating plantar facitis. The securing mechanism is flexible in at least one area above the foot bed to allow for adjustable degrees of dorsiflexion while preventing plantar flexion past the fixed angle of the inclined foot bed.

Removable wedge foot bed inserts result in foot beds that are less than 90° in relation to the upper portion. An angle between 75° and less than 90° has been found to be an optimal range. The device for treating plantar facitis can be made from a variety of sizes of portions. The combination of variously configured portions and variously configured wedge foot bed inserts can be combined to achieve orthotics having desired shapes, sizes and other characteristics. In some embodiments, various desired positions of the foot can be further achieved by a rear heel cup that is positioned to receive and hold various foot positioning devices, which can provide both cushioning and support to the foot being held within the device.

The present invention may be formed in various sizes and shapes according to the traditional shoe sizes that are required and utilized in the prior art. The sizes correspond to U.S. shoe sizes, as described in the Description Of The Preferred Embodiments section contained herein. It is important that the correct size be selected so that the shape of the device is properly proportioned to the length of a person's lower leg. By properly sizing the device, the heel can be secured in a floating position so that it does not touch the foot bed. This device can also be configured with a removable wedge foot bed insert which is higher on one side of the removable wedge foot bed insert than on the other side. This results in inversion or eversion of the patient's foot when placed in the device. A range of greater than 0° and inclusive of 15° has been found to be an optimal range for inversion or eversion.

Another aspect of the invention is a method for treating plantar facitis. The method consists of securing the upper portion of the present invention to the lower posterior portion of the leg and foot of a patient. The method also includes inserting a removable wedge foot bed insert that is inclined from a heel portion of a foot bed to a toe portion of the foot bed, and which forms an inclined foot bed in the lower portion. This inclined foot bed prevents plantar flexion of the foot, and induces dorsiflexion of the foot.

The lower portion that is pivotally attached to the upper portion may then be adjustably locked into various positions to achieve a desired amount of flexion of the foot with regard to the lower portion of the leg. These portions are secured to the leg and foot by means of a securing mechanism that is flexible in at least one area above the foot bed to allow for adjustable degrees of dorsiflexion while preventing plantar flexion past the inclined foot bed. The combination of interchangeable foots beds and variously selecting the angle of orientation between the upper and lower portions allows the adjustable foot beds to be varied so as to accommodate the various modifications and orientations which are desired by a user.

Another aspect of the invention is a method for treating plantar facitis whose steps include inserting a removable wedge into a foot bed portion of a foldable night splint, the foldable night splint having an upper and a lower section held in a hinged interconnection. Both the upper and the lower sections have a generally U-shaped cross-section. The upper section is designed to generally conform to the lower portion of a human leg. The lower section is designed to receive a bottom surface of the patient's foot, as well as to hold a desired shaped wedge within the device. The wedge is also configured to support a bottom surface of a foot, and is inclined from a heel portion to a toe portion. The wedge, therefore, forms an inclined foot bed which prevents plantar flexion. Another step in the method is securing the upper section to the lower posterior portion of a leg and foot of a patient using a securing mechanism that is flexible in at least one area above the foot bed to allow for adjustable degrees of dorsiflexion, while preventing plantar flexion past the desired positioning of the inclined foot bed.

Another aspect of the invention is that the foldable orthosis includes a generally curved portion that is configured to receive a portion of a lower leg and that also is configured to maintain the lower portion of the device in a desired amount of dorsiflexion with regard to the lower portion. In addition to this feature, the angle between the upper and lower portions of the device can be modified and held in a desired orientation by the insertion of spacing devices between the heel locking portions of the upper and lower sections. These spacing devices can be utilized to vary the positioning of the upper and lower heel portions and thus the designated amount of flexion which a patient's foot can be oriented.

The lower portion of the orthotic has a heel section and a toe portion, and extends at an angle of less than 90° from the upper section when the foldable portion is fully flexed and extended. When this device is fully flexed and extended, this configuration is locked into a static alignment, and will not allow the device to move beyond this extended position. This prevents the foot of the person wearing the device from extending downward and shortening the Achilles tendon, rather the present device allows the tendon to be held in a strengthened and lengthened position.

Depending upon the necessities of the various users, varying degrees of extension and flexion for locking the device may be utilized. The lower section also has a generally flat foot bed portion, with the heel portion narrower than the toe portion and designed for close anatomical fit with the heel of a human patient. The lower section is configured to contain both a foot and a foot wedge bed. The lower section also has sides that extend with sufficient height so as to provide the designated amounts of support to the foot of the individual that is utilizing the device.

The upper section is configured for close and anatomically conforming to the lower posterior portion of the human leg. The upper section also includes a sagital concavity that conforms to the human leg and maintains the human heel in a floated position from the flat foot bed. This floated position of the heel is achieved by securing the leg in the upper portion against the sagital concavity. The upper portion has a length that corresponds with the distance from the patient's heel to a point below the thickest portion of the gastrosoleus muscles. The length of this upper portion is designed to provide optimal support to the leg and muscles involved and to reduce pressure points. When extended, the upper and lower portions of the device are configured to substantially cover the heel of the individual utilizing the device.

The lower portion is configured to be about the same length as the foot of the patient. Typically, the upper portion is relatively shorter than the lower portion. The lower portion is designed to receive a removable foot bed insert. In the preferred embodiment, the upper and lower portions are covered with a soft covering that cushions the leg of the user from contact with the generally inflexible materials that make up the upper and lower sections of the device. This configuration of the device also includes a removable wedge foot bed insert that is typically inclined from a heel portion to a toe portion of the foot bed. It therefore forms an inclined foot bed which prevents plantar flexion of the foot. The removable wedge foot bed has a cushioning top surface that is soft and flexible, and also contains a semi-rigid material to which the cushioning top surface is attached. The device also includes a soft jacket that covers the inside and outside surfaces of the upper and lower portions to which the securing device is attached. The securing device is flexible in at least one area above the foot bed to allow for adjustable degrees of dorsiflexion, while preventing plantar flexion past the inclined foot bed. Removable wedge foot bed inserts can be designed to result in a foot bed orientation from less than 90° to 75°. In addition, to the removable foot wedges providing desired foot and lower leg positioning, the inclusion of spacers together with the foldable lockout joint allow the devices to be adjustably locked into desired positions and configurations.

The present invention provides a device that is substantially more versatile than other devices and methods which exist in the prior art and which is also more efficient and cost effective than other devices that are found in the prior art. The present invention through the use of the pivotable and therefore selectively adjustable upper and lower portions enable a practitioner to use a single device that can be modified to meet the needs of a variety of particular patents. This allows a health care practitioner to forgo the expensive costs of individually casting the lower legs and feet of each and every patient, for each and every change in treatment and allows a more flexible and cost effective approach. The present invention allows a practitioner to select a device that is sized according to the foot of the patient, and then to modify that device through the use of spacers between the upper and lower portions of the device, and wedges within the foot beds achieve a desired fit for the patient. As the treatment of the party progresses, rather then creating new casts for the desired position, the brace and the wedges can be modified to accommodate these desired changes. It is estimated that the use of such a device could result in savings of up to eight hundred dollars ($800.00) per patient as compared to the use of the custom casting devices.

In another aspect of the invention, the invention consists of a method for treating plantar facitis in a human patient that includes the steps of inserting a removable wedge into a foot bed portion of a foldable orthotic having an upper and a lower portion. Each of these portions having a generally U-shaped cross-section, with the lower portion also having a heel portion and a toe portion, and being narrower in the heel portion than in the toe portion to facilitate a close anatomical fit to a human foot. The lower portion extends at an angle of less than 90° from the upper section when the two sections are fully extended to a lock out position and has a generally flat footbed portion. The upper and lower sections are also configured to connect with spacing portions which are configured to allow the degree of extension between the upper portion and the lower portion of the device to be varied.

The upper section is designed for close anatomical conformance to the lower portion of a human leg below the thickest part of the patient's gastrosoleus muscle. This portion is covered with a soft covering on its inside and outside surface. The wedge is typically inclined from a heel portion of the foot bed to a toe portion of the foot bed, and thus forms an inclined foot bed that prevents plantar flexion.

Another step of the method is securing the device to the lower posterior portion of a leg and foot using a securing mechanism which is flexible in at least an area above the foot bed. This flexibility allows for adjustable degrees of dorsiflexion while preventing plantar flexion past the inclined foot bed. Another step of the method is requiring the patient to wear the foldable orthotic, the soft covering and the wedge, secured by the securing mechanism to the lower posterior portions of the leg and the foot, while in a reclining position which can occur during sleep or at other times.

In another aspect of the invention, the invention is a method for preventing hip movement in a human patient and includes the steps of securing the upper portion to the lower limp limb of a patient. The upper portion has an inner and an outer surface and an upper section and a lower section. Both sections have generally U-shaped cross-sectional shapes. The lower section includes a heel portion and a toe portion. The heel portion being narrower than the toe portion for close anatomical fit to a human foot. The lower section extends at an angle approximately less than 90° from the upper section and has a generally flat foot bed portion. The upper section is designed for close anatomical conformance to a lower portion of a human leg and, when worn by a patient, extends from the heel of a patient to a portion upward, then to a point below the gastrosoleus muscle. The lower section is configured to receive a bottom surface of the patient's foot. The upper and lower portions are each covered with a soft covering on at least their inside surface and may be covered on its outside surface in addition.

The next step in the process is securing the lower portion of the device to the lower portion of the leg and the foot of a human patient. This is accomplished through the use of a securing mechanism that is flexible in at least an area above the foot bed to allow for adjustable degrees of dorsiflexion while preventing plantar flexion past the inclined foot bed. Another step in the method is placing the portion with the leg and foot of a patient in a stabilizing cradle and securing the portion in a fixed position in the stabilizing cradle with a means of attachment. This means of attachment can be Velcro® straps, hook and loop fasteners or other conventional means of securement.

The next step of the method is requiring the patient to wear the device and the soft covering. The device is secured to a patient's leg by a securing mechanism to the lower posterior portion of the leg and the foot and the portion attached to the stabilizing cradle with a means of attachment while in a reclining position. Optionally, a wedge may be used in the orthosis.

The method and apparatus of the invention, using the foldable orthotic to hold the foot at an angle of less than 90° to the leg, prevents plantar flexion of the foot and promotes dorsiflexion of the foot without applying pressure to the heel. The orthosis can also be used for post surgery treatment of a foot, leg, and/or hip, to relieve pressure on the area that has been operated on and to immobile areas requiring such immobilization.

Further, the purpose of the foregoing abstract is to enable the United States Patent and Trademark Office and the public generally, and especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

Still other objects and advantages of the present invention will become readily apparent to those skilled in this art from the following detailed description wherein I have shown and described only the preferred embodiment of the invention, simply by way of illustration of the best mode contemplated by carrying out my invention. As will be realized, the invention is capable of modification in various obvious respects all without departing from the invention. Accordingly, the drawings and description of the preferred embodiment are to be regarded as illustrative in nature, and not as restrictive in nature.

DESCRIPTION OF THE PREFERRED EMBODIMENTS

Figure 1:
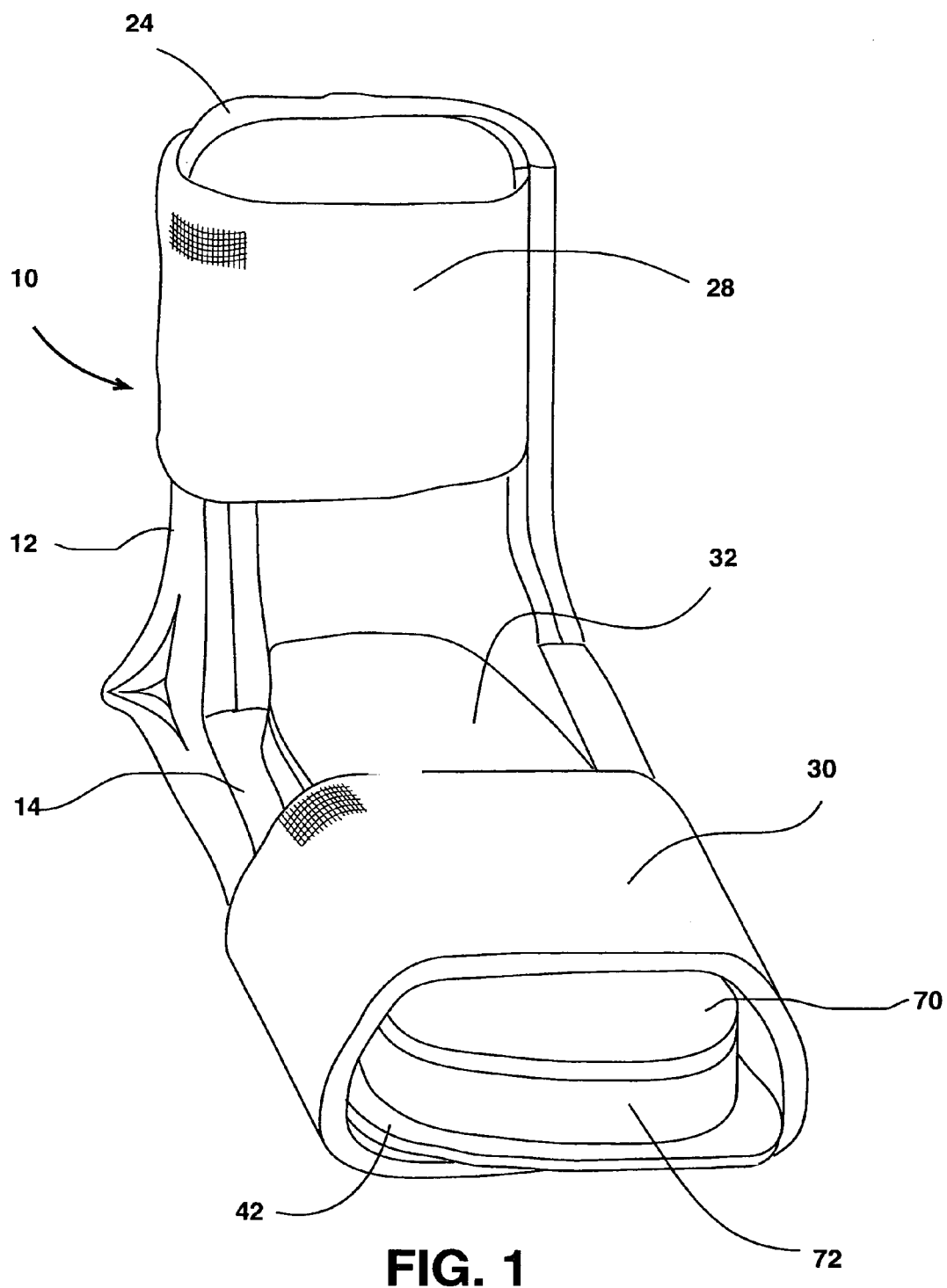
FIG. 1 is a perspective view showing the ankle foot orthosis.

While the invention is susceptible of various modifications and alternative constructions, certain illustrated embodiments thereof have been shown in the drawings and will be described below in detail. It should be understood, however, that there is no intention to limit the invention to the specific form disclosed, but, on the contrary, the invention is to cover all modifications, alternative constructions, and equivalents falling within the spirit and scope of the invention as defined in the claims.

Referring to FIGS. 1 through 9, the ankle foot orthosis of the present invention is shown to advantage. FIG. 1 shows the ankle foot orthosis 10 which is configured for connection with a lower leg and foot of a patient. The ankle foot orthosis 10 comprises a foldable shell 11 having an upper portion 12 that is pivotally connected to a lower portion 14 through a hinge 16 (shown in FIG. 2). A jacket, which according to the depicted embodiment comprises a fabric covering 24, covers the inside and outside surfaces of the upper and lower portions 12, 14. A removable wedge foot bed insert 32 is configured to provide a desired level of plantar and dorsiflexion to the individual. In addition, a lower leg attachment strap 28 and a foot attachment strap 30 provide means for attaching the device 10 to the foot and lower leg of a patient. The fabric covering 24 surrounds and covers selected portions of the inside and outside surfaces of upper and lower portions 12, 14.

In this preferred mode, removable wedge foot bed insert 32 is composed of two layers of foam, a soft-top layer 70, and a firm foam layer 72. In the preferred mode, soft top layer 70 is made of Sentinel Blue F-Cell MTL foam, a cross-linked polyethylene foam. However, another soft material could also be utilized. Firm foam layer 72 is preferably Sentinel White MTL F-Cell AW900, a cross-linked polyethylene foam. However, other materials could be utilized that provide support and resist deformation. In the preferred embodiment, removable wedge foot bed insert 32 fits the flat foot bed 42 of the lower portion 14. This means that removable wedge foot bed insert 32 is narrower at the heel portion 46 than at the toe portion 48. A variety of foot bed angles can be formed from removable wedge foot bed inserts 32 of varying angles. Other embodiments of the preferred mode may utilize removable foot bed inserts 32 which vary in thickness from one side to another, as will be discussed later.

Fabric covering 24 is provided with a lower leg attachment strap 28 and a foot attachment strap 30, which attaches the device 10 to a patient's leg and foot with a plurality of hook type fasteners so as to provide easy attachment and detachment of the device from a desired location along the foot of a user. While hook type fasteners are shown, it is to be distinctly understood that other types of devices for fastening a device or means of fastening can be utilized, such as the use of straps and buckles, metal loops to pass straps through, and any conventional means of attachment.

Figure 2:
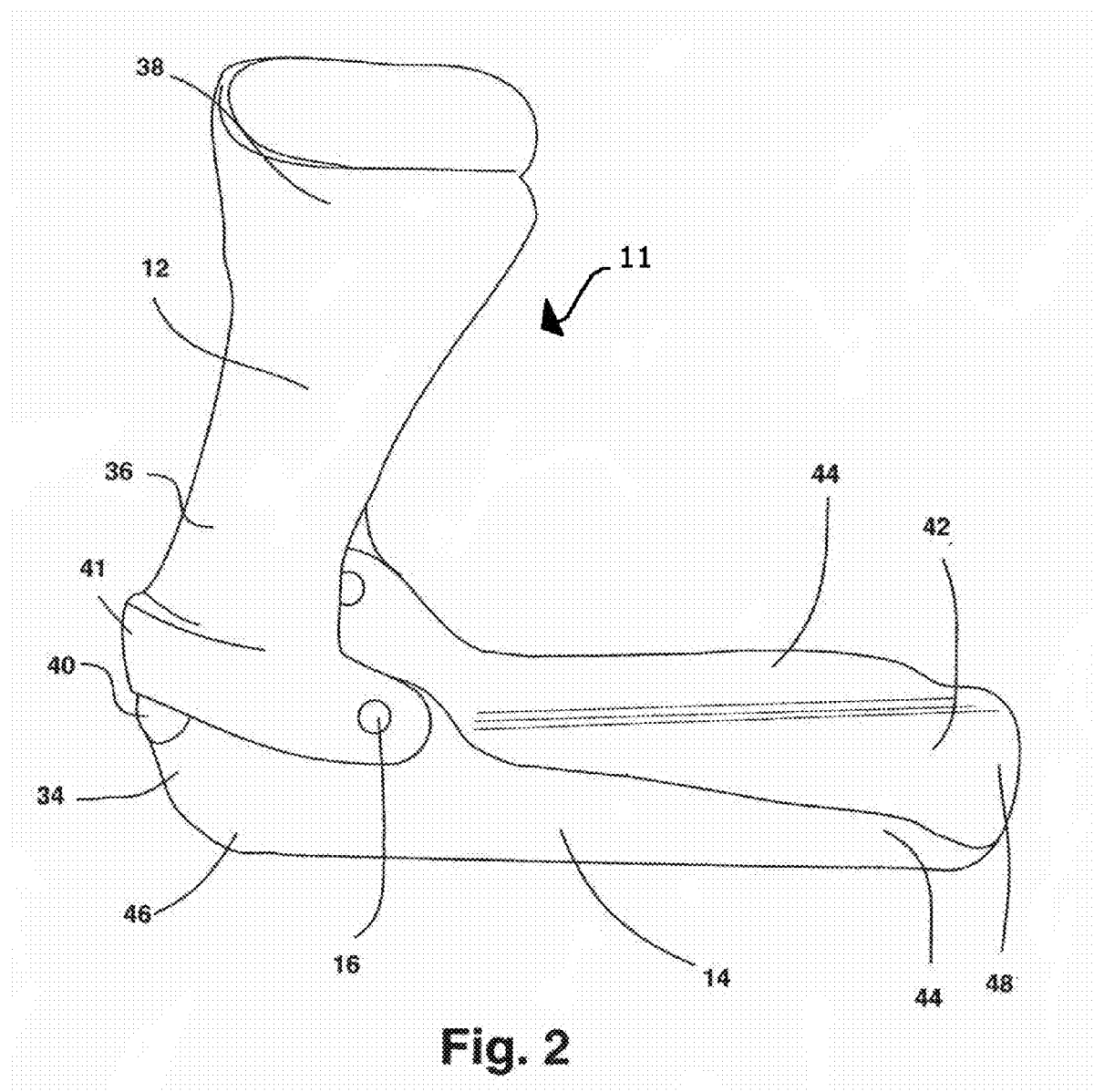
FIG. 2 is a perspective representational view of the upper and lower portions of the ankle foot orthosis when fully extended.

Referring now to FIG. 2, the internal structure of the device 10 is shown. The portions of the device 10 are comprised of an upper portion 12, and a lower portion 14. These portions 12, 14 are pivotally connected to each other through a hinge 16. In the preferred mode, the portion 12, 14 are made up of plastic, although other materials could be utilized. In the preferred mode, lower portion 14 and the upper portion 12 are configured to extend apart from one another to reach an angle at their greatest degree of separation of approximately 80°-85°. This angle of separation is achieved by the interlocking of the portions 41, 40 of the device. The interlocking of these portions prevents the upper and lower sections 12, 14 from extending apart from each other any further.

The upper portion 12 and lower portion 14 each have a cross-section that is generally U-shaped and are configured to accommodate the respective anatomical portions of the individual wearing the device as well as other items such as removable foot wedges and other such devices. Preferably, the upper portion 12 is shorter in length than the lower portion 14.

Upper portion 12 is shaped to closely follow the contours of the posterior of a patient's foot and lower leg. It contains a sagital concavity 36 and a leg flare 38 that are configured to receive and hold desired portions of an individual's leg therein. These portions 36, 38 are also configured to maintain a desired amount of dorsiflexion upon the foot of the person wearing the device. The lower portion 14 is configured to follow the contours of the posterior and lower portions of a patient's foot. The lower portion has a heel pocket 34 that further provides a rear heel cup 40 and a foot bed 42, which is configured to receive an orthopedic wedge having a desired shape and orientation as well as the foot of an individual. In this preferred embodiment, when the upper and lower portions are fully extended, the heel of the individual is fully enclosed. The foot bed 42 also has side pieces 44 that run along each side of the foot bed 42. Flat foot bed 42 has a heel portion 46 and a toe portion 48. The foot bed 42 is narrower at the heel portion 46 than at the toe portion 48 to accommodate the typical contour of a human foot.

Figure 6:
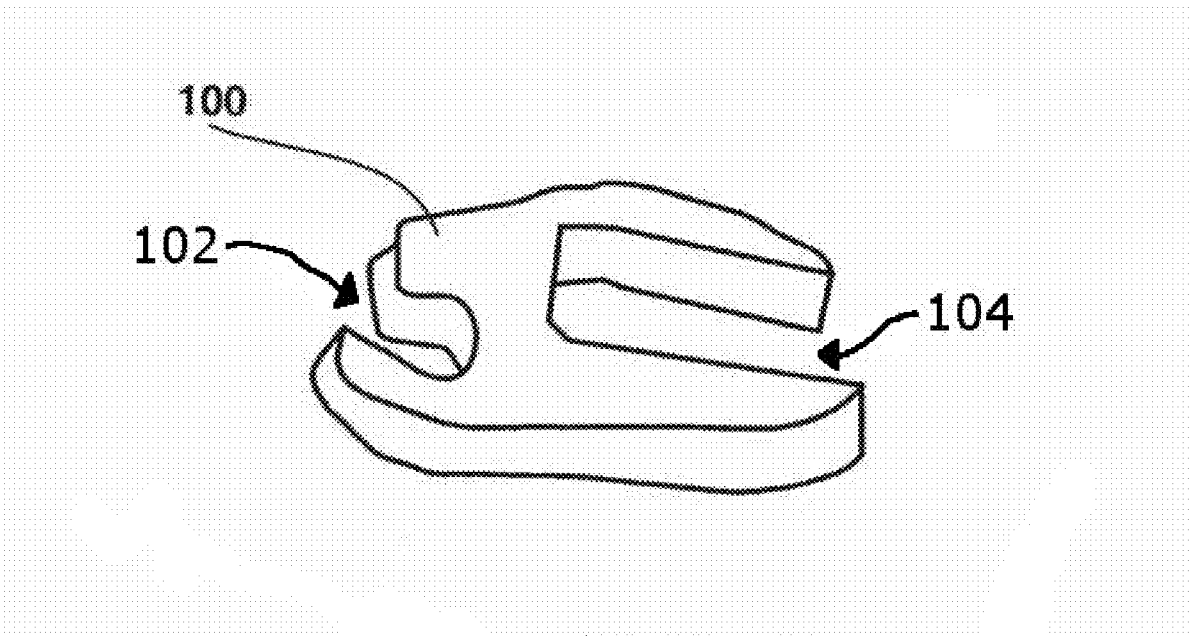
FIG. 6 is a bottom perspective view of a spacer device that is configured for use in the present invention.
Figure 7:
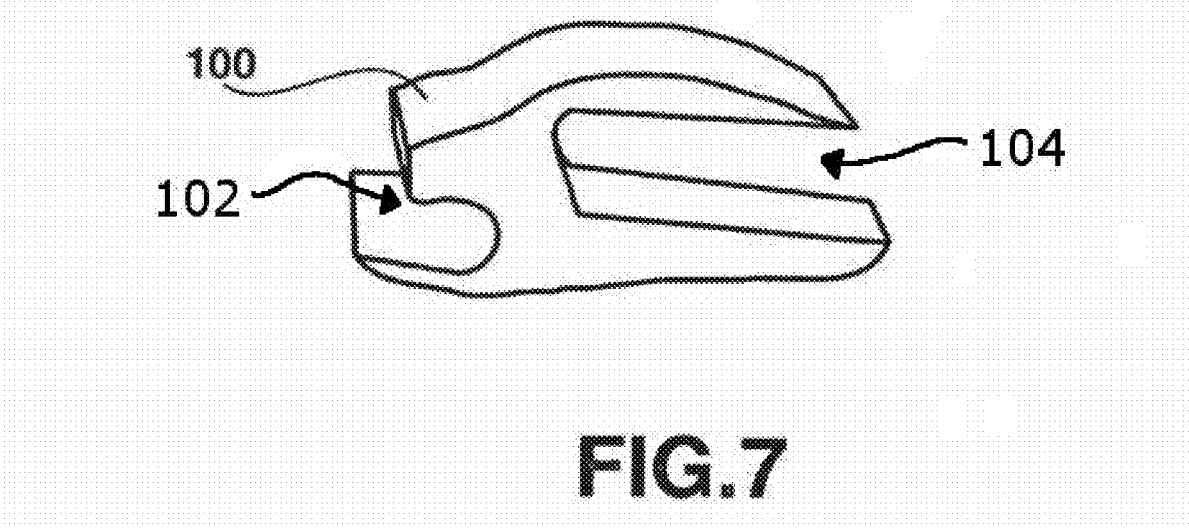
FIG. 7 is a top perspective view of the spacer device shown in FIG. 6.

Near the hinge portion of the device 16, where the upper portion 12 and the lower portion 14 intersect, the upper and lower portions of the device are flared so as to provide a desired amount of space for the brace 10 to extend around the ankle protrusions of the patient. In addition a ridge 41 is formed within the upper portion 12 of the device so as to interact with the heel cup portion 40 so as to allow the upper 12 and lower 14 portions of the device to be locked in a designated position. This junction is a relatively static type of union that prevents a patient's foot from significant alteration from this designated position. A variety of spacers 100, preferably rubber spacing blocks such as those shown in FIGS. 6 and 7 provide increased variations in the positioning of the upper and lower portions of the device. These spacing blocks function to limit the extending angle that the upper 12 and lower 14 portions of the device that the device may be extended to.

Figure 3:
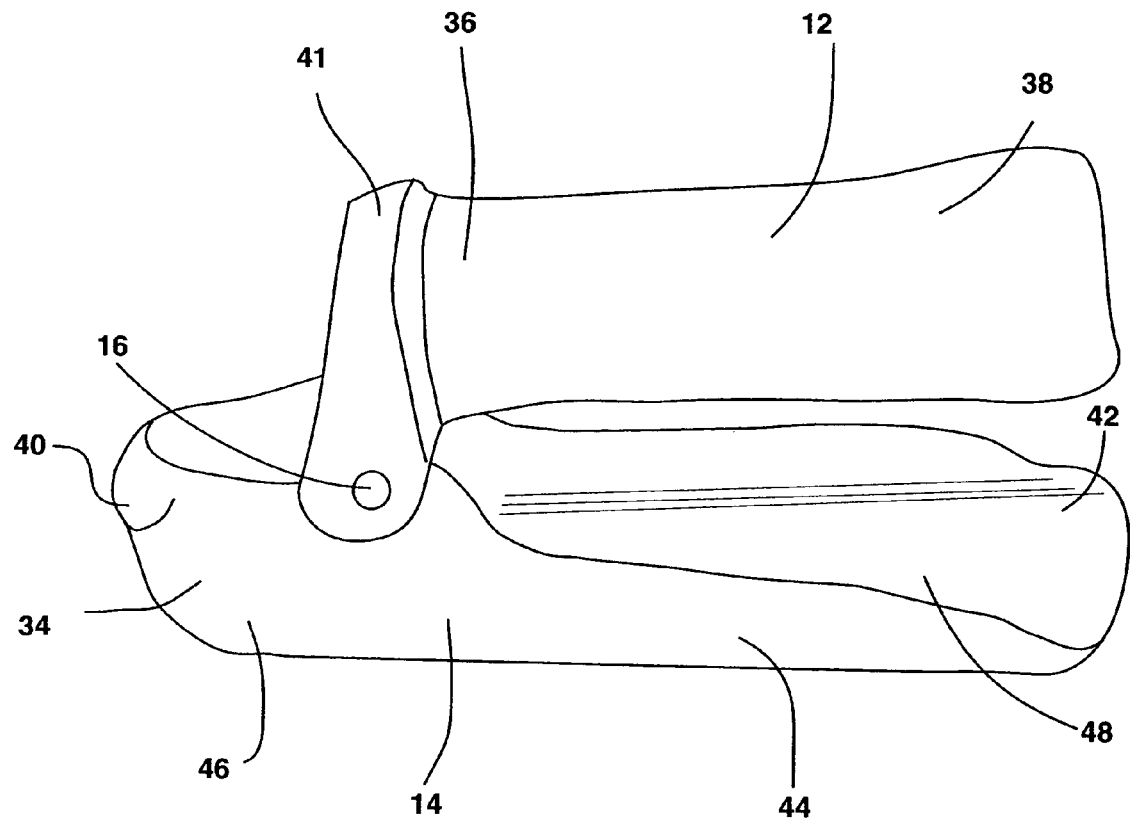
FIG. 3 is a side representational view of the embodiment shown in FIG. 2 in a folded position.

Referring now to FIG. 3, a side view of the embodiment shown in FIG. 2 is shown in a folded, or compacted position. In this position, the device 10 can also be stored in a variety of containers, including, but not limited to, a standard shoe size box. This feature also allows the present device to be transported to a variety of locations and increases the likelihood that an individual will actually use the device to obtain the desired therapeutic effects. An end view of this embodiment is shown as FIG. 4.

Figure 4:
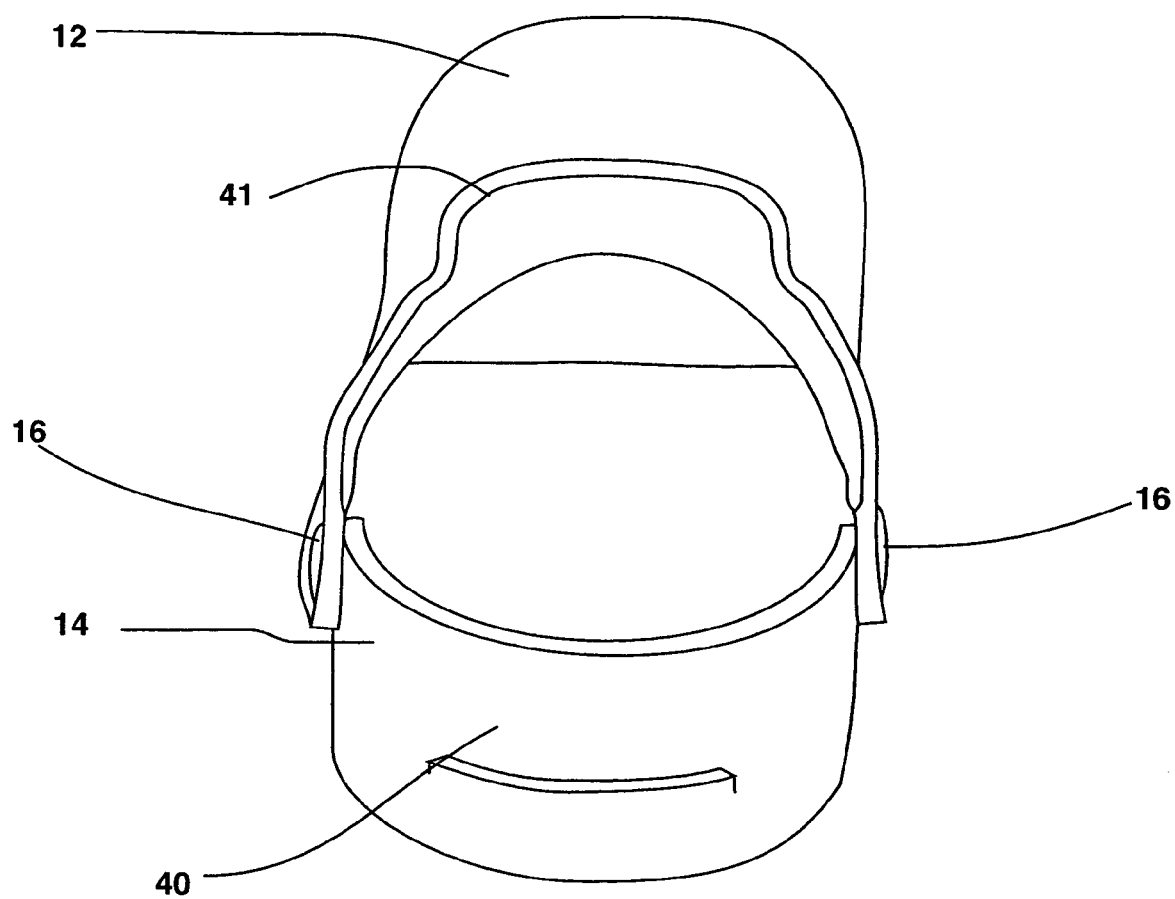
FIG. 4 is a rear view of the embodiment shown in FIG. 3.

FIG. 4 shows an end view of the preferred embodiment of the invention when the invention is in a folded position. In this position, the ridge 41, which is defined within the upper portion 12, is not in contact with the heel cup portion 40. In this folded position, the device 10 is configured for placement and insertion with a storage container such as a standard sized shoebox.

The angle of extension between the lower portion 14 and the upper portion 12 can be varied by the placement of spacers 100 between the upper 12 and lower 14 portions. These spacers can be inserted between the upper 12 and lower portions 14 so as to hold the device in a desired position and orientation. When these spacers are used in such a manner, the positioning and orientation of the upper 12 and lower 14 portions of the device can be modified and oriented so as to achieve a desired amount of dorsiflexion in the foot of the user. In addition to modifying the angle of extension between the upper 12 and lower 14 portions of the device 10, the angle of dorsiflexion for a foot can also be variously modified by varying the wedges within the device as well as the amount of curvature within the upper portion 12 of the device.

Figure 5:
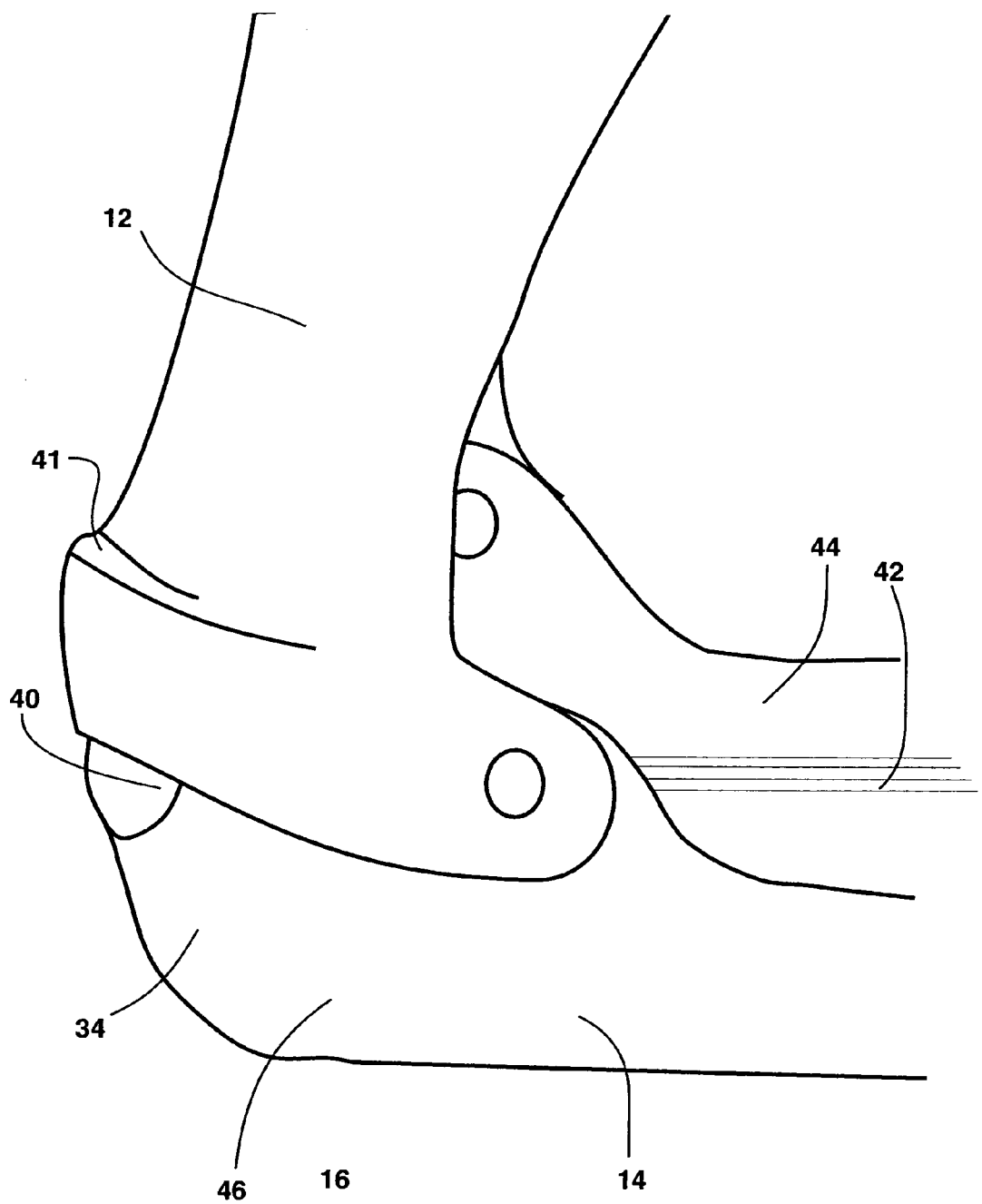
FIG. 5 is a detailed view of the connection portion of the device shown in FIG. 4.

FIG. 5 shows a detailed side view of the embodiment of FIG. 2 wherein the connection between the upper and lower sections 12, 14 are shown to advantage. The maintenance of the upper section 12 in a desired position with regard to the lower portion 14 is accomplished by the intersection of a ridge 41 that is located within the upper portion of the device 12. This ridge 41 is configured to intersect with a portion of the lower portion 14 so as to hold the upper and lower portions 12, 14 of the device in a position of maximum desired extension. While in this preferred embodiment the angle of extension between the upper portion and the lower portion is about 80°. It is to be distinctly understood that the angle of extension is not limited thereto but may also be variously configured and embodied to a variety of angles depending upon the desires of the healthcare practitioner related to the party at issue. In addition, while this type of locking feature is shown in this preferred embodiment, it is to be understood that the invention is not limited thereto but may be variously embodied to hold the upper and lower portions of the device in a desired arrangement depending upon the necessities and desires of a user.

Figure 8:
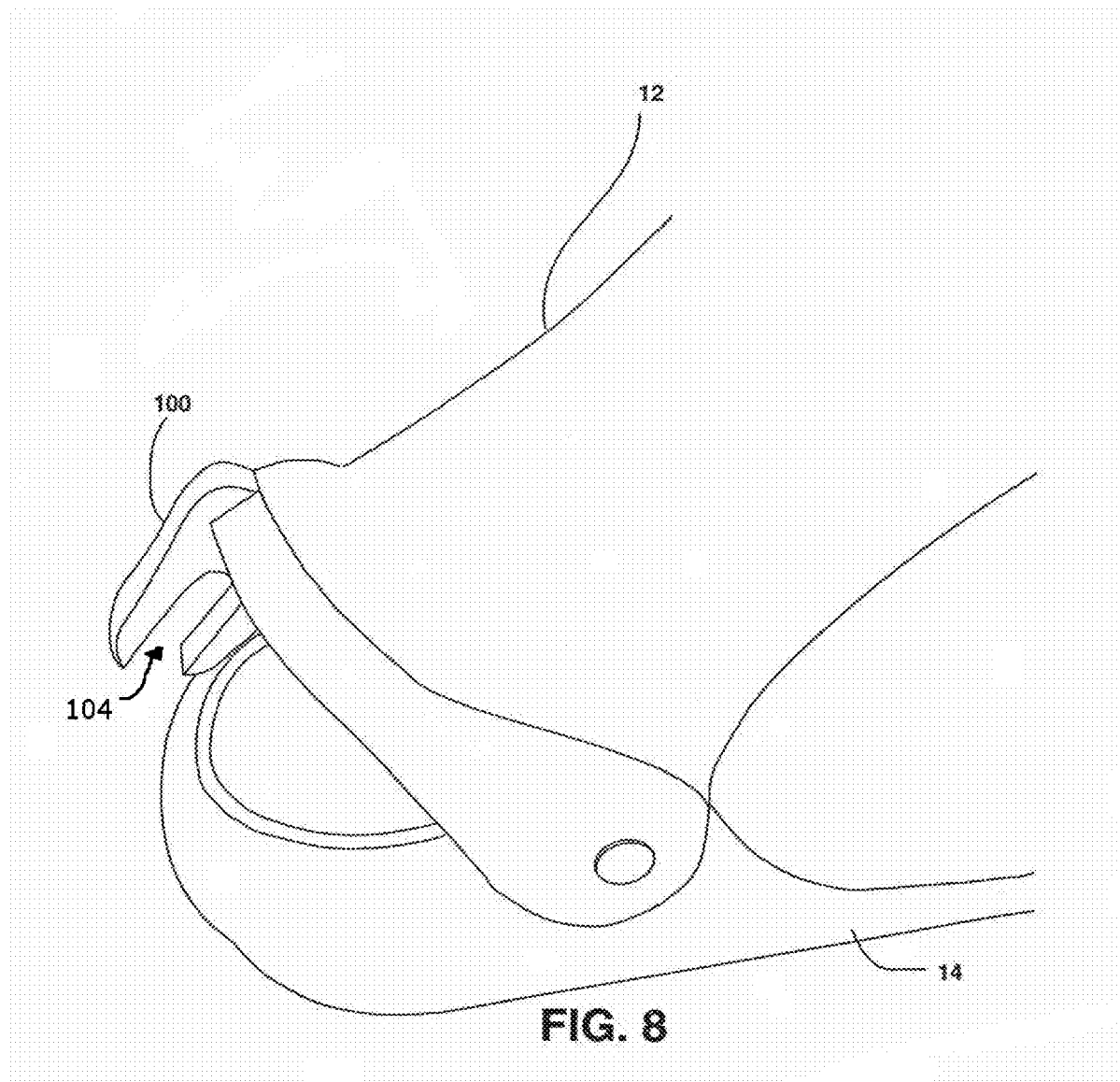
FIG. 8 is a detailed perspective of the foldable orthotic of the present invention used together with a spacer shown in FIGS. 6 and 7.
Figure 9:
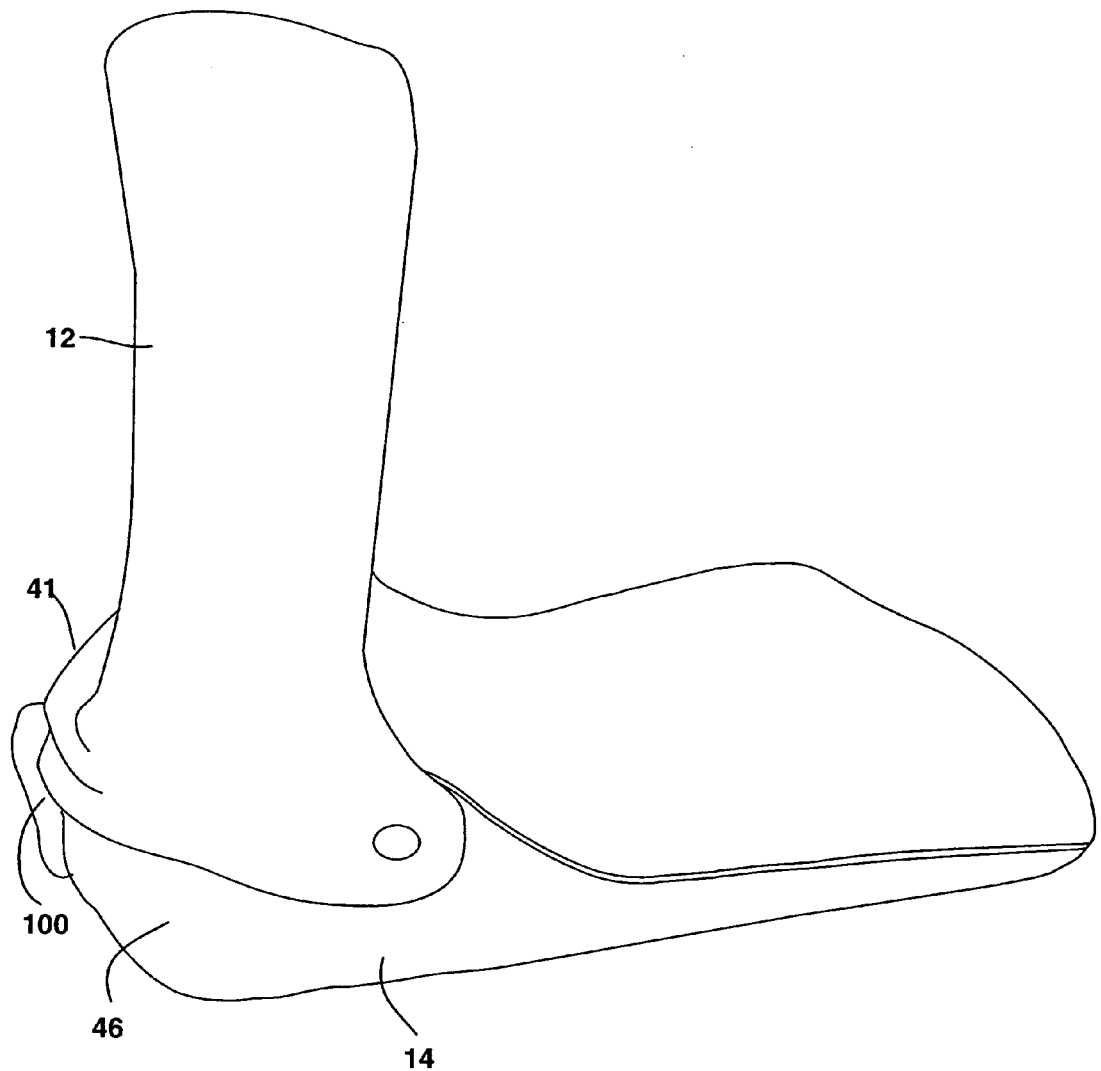
FIG. 9 is a view of the foldable orthotic of the present invention used in conjunction with the spacer.

FIGS. 6 and 7 show views of the rubber spacers 100 of the present invention. The use of these spacers is shown in FIGS. 8 and 9. In certain circumstances the treatment of various conditions requires that various modifications to a traditional night splint take place. Thus, in order to achieve these ends, a splint must be modified so as to allow and provide an increased amount of flexibility in the device itself. The present invention allows for these modifications to take place. The present invention provides a rubber spacer that is configured to fit between the upper and lower portions of a night splint and thus hold the night splint in a desired position and orientation. According to the depicted embodiment, the spacers 100 define a top notch 102 and a bottom notch 104, as shown in FIGS. 6 and 7. The top notch 102 is configured to receive therein a section of the lower edge of the upper portion 12 of the device, as shown in FIG. 8, The bottom notch 104 is configured to receive therein a section of the upper edge of the lower portion 14 of the device, as shown in FIG. 9. This flexibility allows for a variety of treatment to take place and allows a practitioner to modify a single device by changing the positioning and dimensions of the spacers so as to allow and maintain the night splint in a desired position and orientation. This allows for a single device to treat a variety of conditions, such as: Neoplasms of the short bones of lower limb, other benign neoplasm of the connective and other soft tissue of lower limb, including the hip, benign neoplasm of other specified sites, diabetes mellitus with neurological manifestations, gouty arthropathy, physical deformations due to morbid obesity, Neurological conditions such as spastic hemiplegia, cerebral palsy, quadriplegia, tarsal tunnel syndrome, lesion of the plantar nerve, monoeuritis of lower limb, hereditary and idiopathic peripheral neuropathies, unspecified inflammatory and toxic neuropathy.

Inflammatory conditions such as ulcer of heel and midfoot, arthropathy associated with neurological disorders, rheumatoid arthritis, osteoarthritis in the lower leg, ankle and foot, tendonitis, bursitis of various portions of the lower leg, foot and ankle, calcaneal spurs, enethesopathies of various sites, rheumatism, myalgia and myosistitis.

Misalignment conditions such as dislocation of the foot and ankle joint, contracture of the ankle and foot joint, anklyosis of joint, effusion of joint, lower leg, ankle and foot joint, pain in joint, lower leg, ankle and foot joint, fractures, malunion of fracture, non-union of fracture, Treatment of tendon and ligament conditions such as repair and healing of rupture tendons, plantar fascitis, laxity of ligaments, disorders of the synovium, tendon and burs, and Treatment of foot disorders such as Hallux Valgus, Hallux Rigidus, claw toe, other acquired deformity of toe, Genu Valgum, Aquired Equinovarus Deformity, Cavus deformity of the foot, Cavovarus deformity of the foot acquired, other Aquired Calcaneus Deformity, Talipes Varus, Talipes Equinovarus, Metatarsus Primus Varus, Metatarsus Varus, Talipes Cavus, other deformities of foot and limb, and loose connective tissue disorders such as Ehlers-Danlos Syndrome.

Each of these types of therapies requires the specific use of specific foot and lower leg positioning based upon the underlying pathology. The present invention with its adjustable and variable positioning features allows a podiatrist to respectively, stretch, contract, and immobilize the joints and areas upon which the device is placed. This is a significant advantage over the prior art which required separate plaster castings to be done in order to cause this action to take place.

Figure 10:
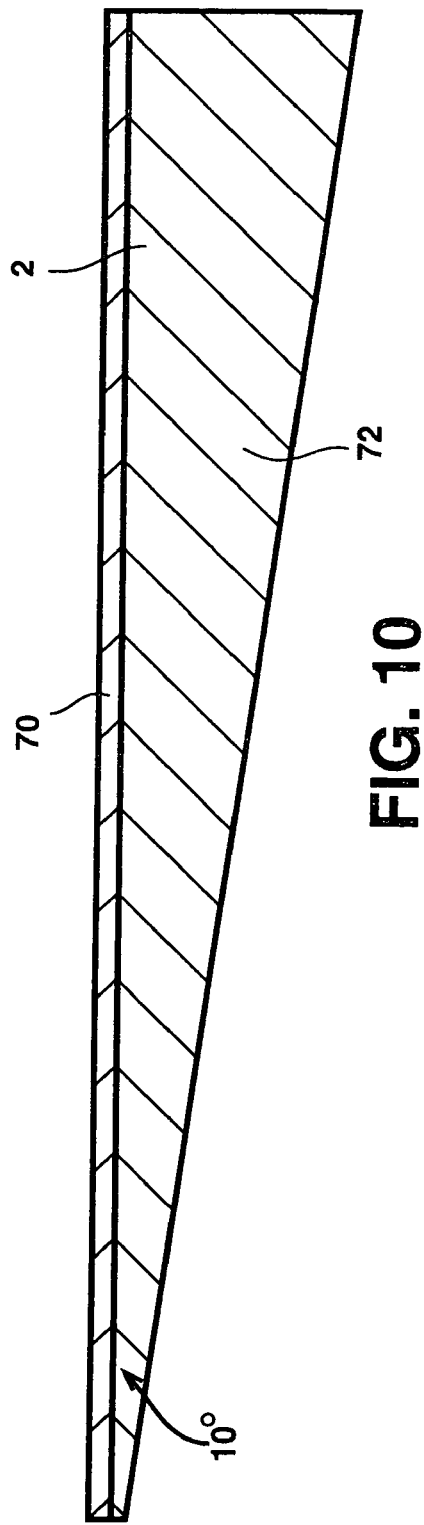
FIG. 10 is a side plan view of a 10° removable foot bed wedge insert.
Figure 11:
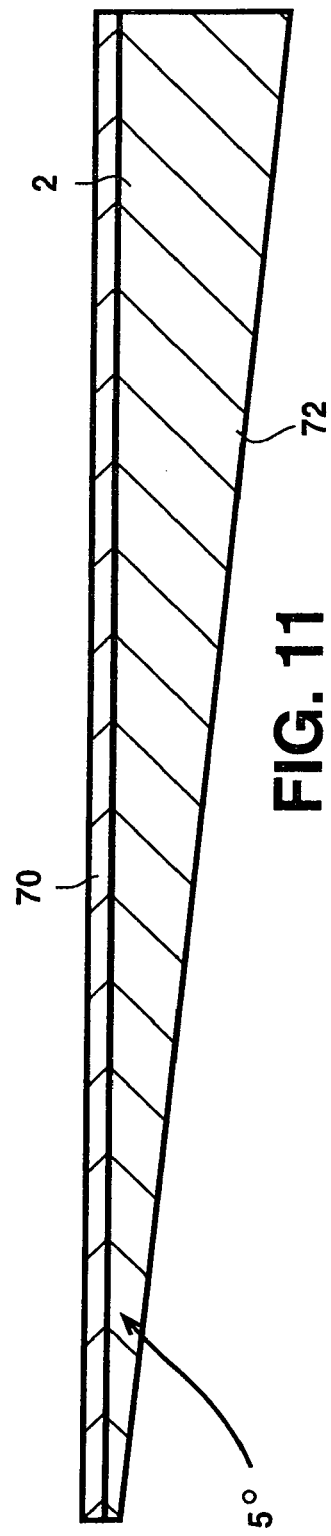
FIG. 11 is a side plan view of a 5° removable foot bed wedge insert.

FIGS. 10 and 11 show two variations of removable wedge foot bed inserts 32. FIG. 10 shows a 10° wedge for use with ankle foot orthosis 10 and FIG. 11 shows a 5° wedge for use with ankle foot orthosis 10.

Figure 12:
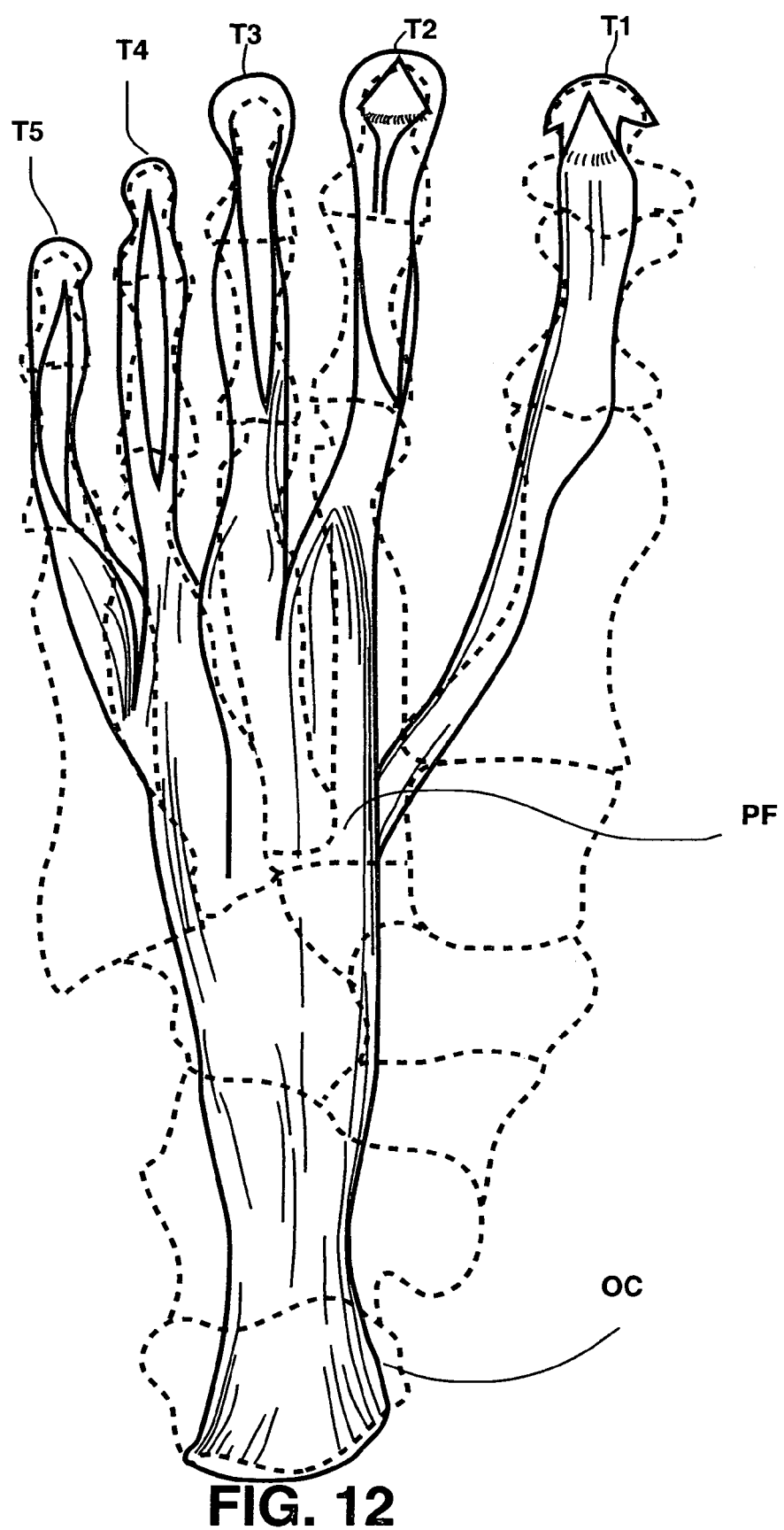
FIG. 12 is a dorsal or bottom anatomical plan view of a human foot.

FIG. 12 shows a bottom view, or plantar view, of the human foot depicting the plantar facia PF attaching at the heel bone, or os calcis, extending longitudinally across the bottom of the foot, and eventually dividing near the heads of the metatarsal bones into five processes, with one process attaching to each of the five toes, T1 through T5.

Figure 13:
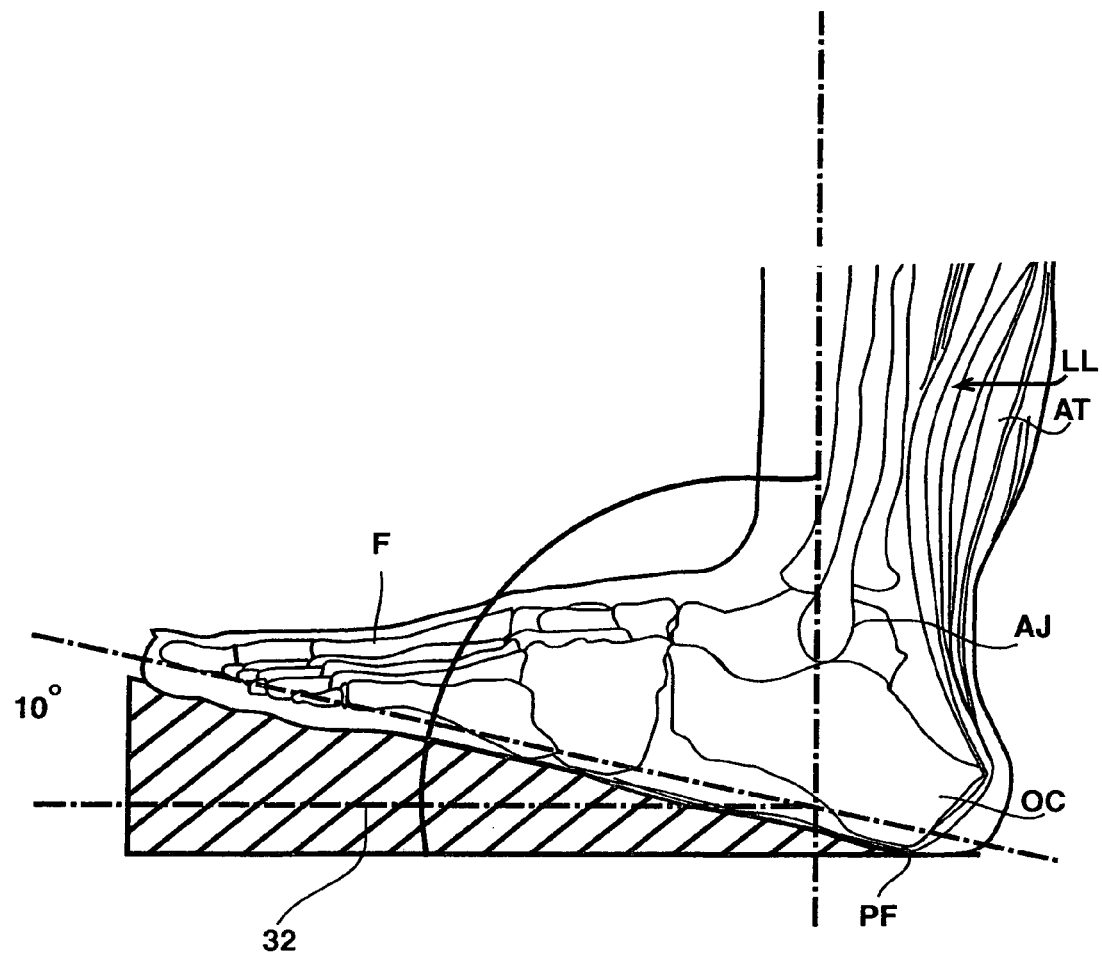
FIG. 13 is a side view of a human foot and a removable foot bed wedge insert.
Figure 14:
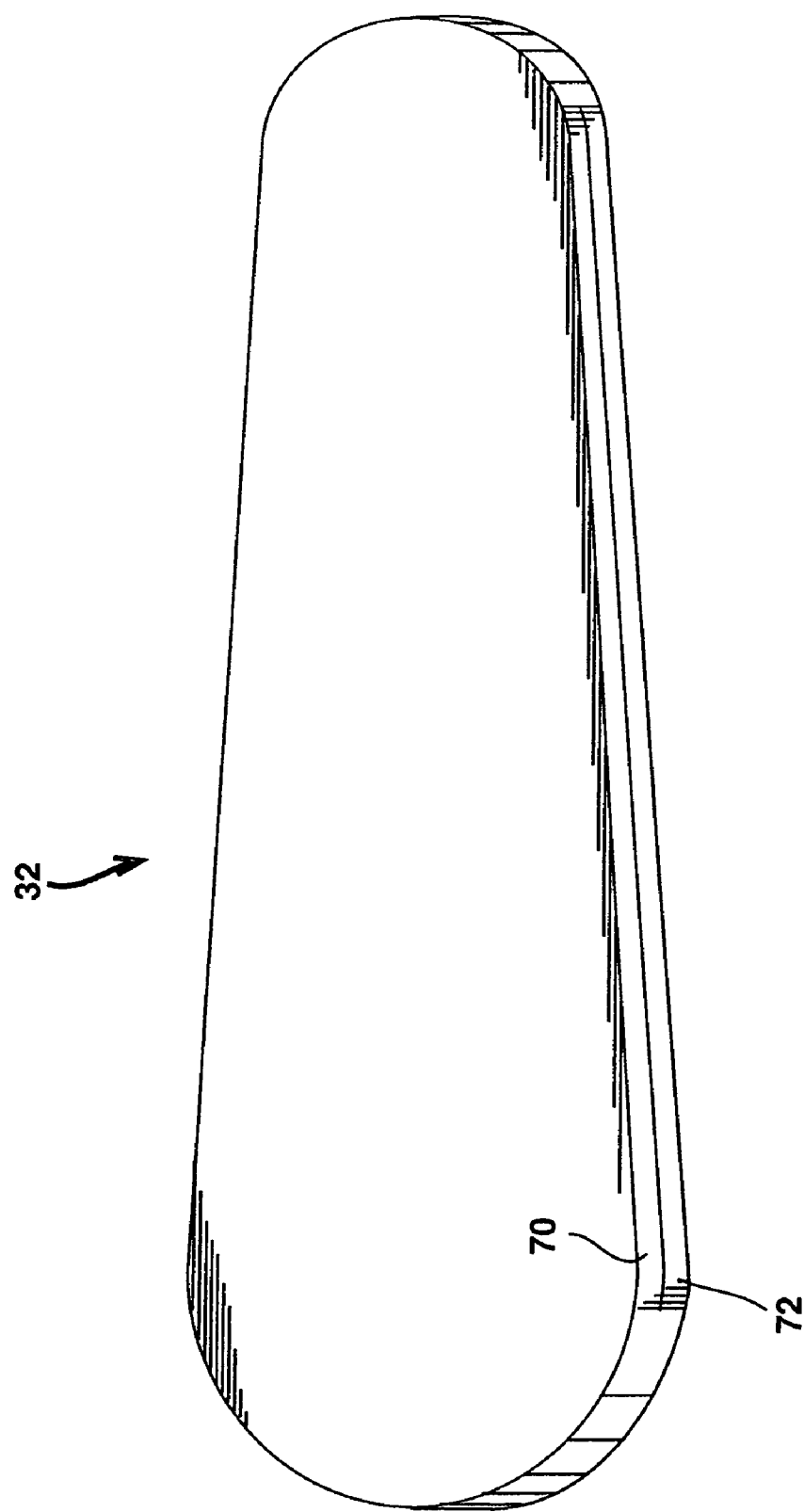
FIG. 14 is a representational view of a removable wedge which when used with the orthosis would result in inversion or eversion of the patient's feet.

FIG. 13 shows ankle joint AJ formed by the articulation of foot F with lower leg LL, specifically the articulation of the tibia and the fibula, the two bones which comprise the skeletal frame of the lower leg and the astragalus, the largest of the tarsal bones located next to the os calcis. FIG. 13 also shows ankle joint AJ in 10° dorsiflexion. The dorsiflexion in this instance is caused by removable wedge foot bed insert 32 having a 10° incline. Use of this wedge foot bed 32 in conjunction with the other portions of the orthotic 32 results in a foot bed which is positioned 80° in relation to the angle of the upper section 12 of the orthosis 32.

FIG. 13 also shows the attachment of the plantar facia to the inner tubercle of the os calcis OC and the plantar facia PF extended slightly by the dorsiflexion of the ankle joint AJ. FIG. 13 also shows Achilles tendon AT.

In use, initially, a choice of incremental size of ankle foot orthosis 10 is made selecting a size which most closely conforms to the patient's foot and leg size. The present configuration of ankle foot orthosis 10 has sizes pediatric, small, medium, large, and extra large, which correspond to men's and women's shoe sizes as shown below:

| | |
|---|---|
| Pediatrics: | Women's: smaller than 4 |
| | Men's: smaller than 7 |
| Small: | Women's: 4-6 |
| | Men's: 7-9 |
| Medium: | Women's: 6-8 |
| | Men's: 9-11 |
| Large: | Women's: 8-10 |
| | Men's: 11-13 |
| Extra Large: | Women's: 11 and larger |
| | Men's: 14 and larger |

Next, referring to FIGS. 1 through 14, a removable wedge foot bed insert 32 of a desired angle is chosen and inserted into the foot bed 42 of the ankle foot orthosis 10. The chosen wedge 32 can be used to cause dorsiflexion or plantar flexion of the foot, and can also result in inversion or eversion of the foot in relation to the leg. A patient's lower leg LL and foot F are placed into the ankle foot orthosis 10 so that the foot F rests comfortably on the soft top layer 70 of the chosen removable wedge foot bed insert 32. Lower leg attachment strap 28 is passed from one side of upper portion 12 to the other side, across the lower leg LL. Similarly, the foot attachment strap 30 is secured across the patient's foot F. After securing the patient's foot, the patient's heel is in a floating position, and is not touching the flat foot bed 42 or the removable wedge foot bed insert 32. This floating heel position is maintained by the shape of the sagital concavity 24 and the size of orthosis 20 selected for the patient. The positioning of the heel is further assisted by the rear heel cup 40 that is configured within the lower portion 14 of the device. This heel cup 40 may be configured to be variously shaped and to hold a variety of supportive pieces therein.

Fabric covering 24 of the orthosis 10 is designed to pad the patient's foot from any possible pressure points on the inside of the portions 12, 14. Additionally, the portions 12, 14 are shaped to minimize any possible pressure points. The fabric covering 24 also protects the collateral leg of the patient from being bumped or bruised by contact with the outside of the ankle foot orthosis 10.

The portions 12, 14 are designed to closely follow the anatomical contours of the patient's foot, ankle, and lower leg. This serves two purposes: one is to reduce the number of pressure points on the patient's foot. The other is to use the shape of the orthosis to position the patient's heel in a floating position. Since many patients being treated for plantar facitis may have tender regions on the heel bone or even bone spurs, it is important that any pressure placed on the foot, ankle and lower leg avoid pressure to the heel, while delivering even and comfortable pressure to other parts of the foot, ankle, and lower leg. Pressure must be applied to the front portion of the foot, but not the heel, so that the foot is pressed and held in a dorsiflexed position during sleep.

When ankle foot orthosis 10 is secured to an individual's lower leg and foot as described hereinabove, the ankle joint is preferably placed in dorsiflexion, but certain conditions require the use of plantar flexion, inversion, eversion, or neutral orientation, and these positions are achieved by selecting the pitch of the removable wedge foot bed inserts 32 that are used. A range of dorsiflexion of greater than 0 and inclusive of 15 has proven to be an optimal range for treatment of plantar facitis. When the ankle is so flexed, plantar facia PF and Achilles tendon AT are extended and held in a position of extension so long as the ankle foot orthosis 10 is worn as described herein.

Figure 15:
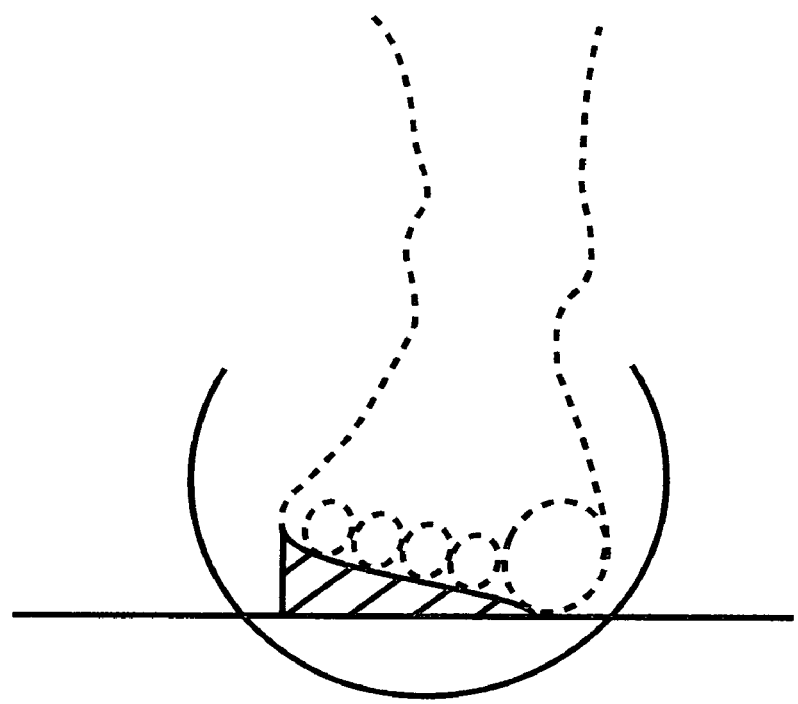
FIG. 15 is a front view of a human foot and a removable foot bed wedge insert in everted configuration.
Figure 16:
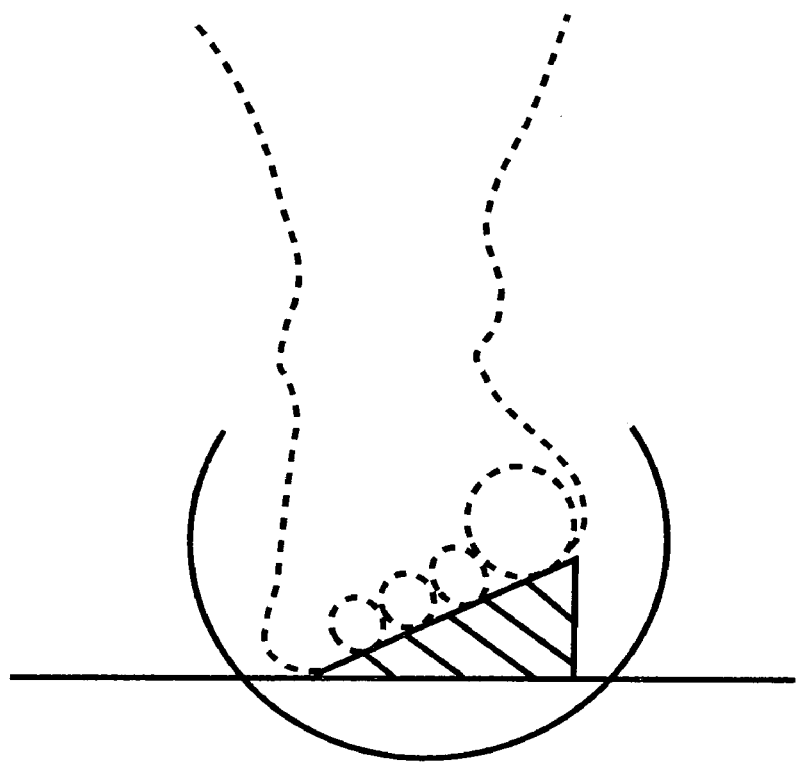
FIG. 16 is a front view of a human foot and a removable foot bed wedge insert in inverted configuration.

Inversion or eversion of the foot may also be desired and achieved by the use of appropriately shaped removable wedge foot bed inserts 32. This may occur after surgery on tendons in the foot. If the tendons worked on are on the medial side of the foot, it is desirable for the foot to be held in an inverted position, with the plantar surface facing toward the midline of the body. This relieves strain on the affected tendons. If the tendons worked on are on the lateral side of the foot, an everted position is desirable. A treatment of gradually changing the angle of the wedges from inverted or everted to neutral, and then gradually decreasing the plantar flexion and then increasing the dorsiflexion can be preferentially selected by physicians. Examples of such inserts are shown in FIGS. 15 and 16.

Plantar flexion can be preferred after foot or tendon surgery, as an acclimatization to gradual stretching and lengthening of the Achilles tendon and plantar fascia by gradually decreasing plantar flexion and increasing dorsiflexion.

Figure 17:
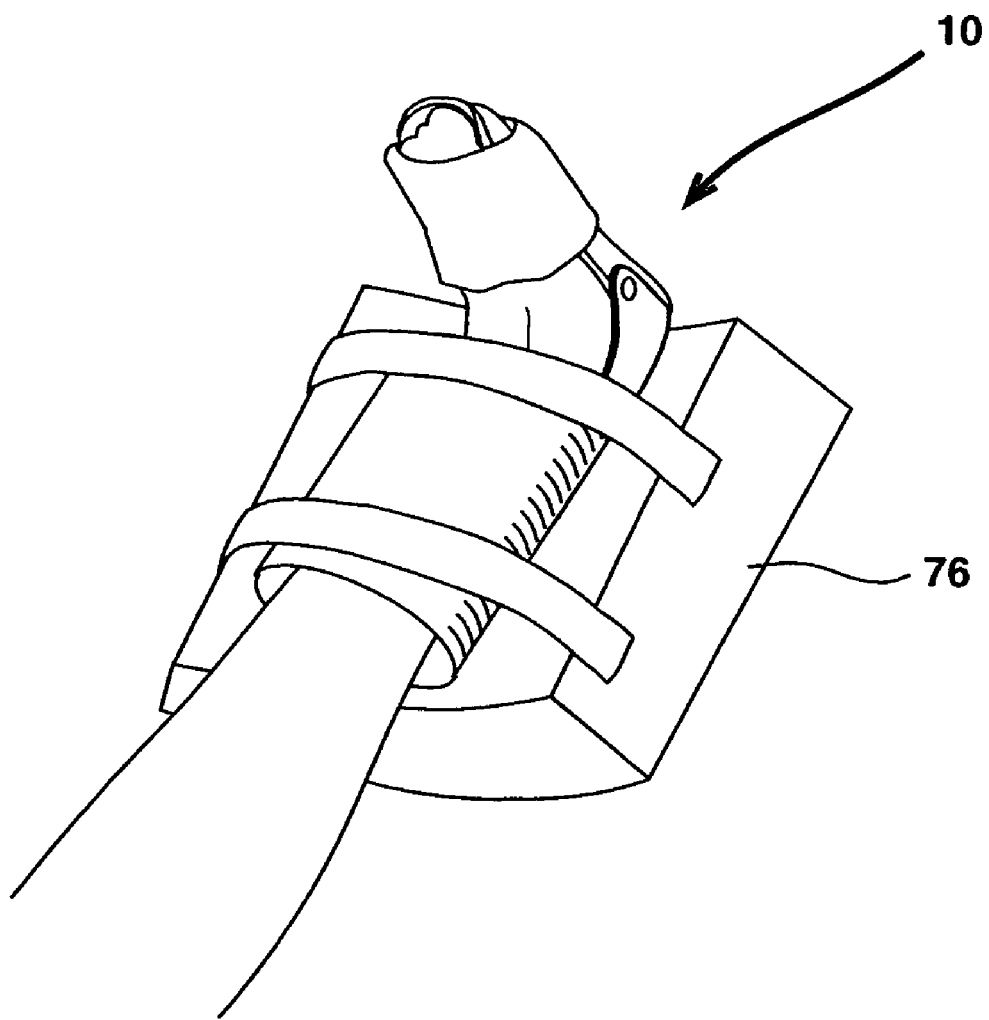
FIG. 17 is a perspective view of an ankle foot orthosis used in conjunction with a stabilizing cradle.

In another preferred embodiment, the ankle foot orthosis 10 is used in conjunction with a stabilizing cradle 76. Stabilizing cradle 76 is a device to which the ankle foot orthosis is attached and secured, as shown in FIG. 17. This mode of operation is indicated for patients recovering from hip replacement surgery or other procedures in which the hip and leg need to be immobilize. With the patient on his/her back, and one or both legs secured in an ankle foot orthosis 10, which is itself secured to a stabilizing cradle 76, the leg(s) is immobilized and the hip joint can heal optimally.

While there is shown and described the present preferred embodiment of the invention, it is to be distinctly understood that this invention is not limited thereto but may be variously embodied to practice within the scope of the following claims. From the foregoing description, it will be apparent that various changes may be made without departing from the spirit and scope of the invention as defined by the following claims.

I claim:

1. A device for treating plantar facitis which comprises:
a foldable orthotic having an upper portion pivotally connected to a lower portion each portion having generally U-shaped cross-sectional profile, said upper and lower portions adjustably pivotally interconnected at a hinged portion and configured to be selectively arranged between a folded position and a first locked extended position of less than ninety degrees, said upper portion configured to generally conform to the lower portion of a human leg, said lower portion configured to receive a bottom surface of a foot attached to said leg, said lower portion containing a heel cup portion, said upper portion defining a ridge, said ridge configured to interlock with said heel cup portion such that, when said foldable orthotic is in said first locked extended position, said heel cup portion and said ridge are statically interlocked such that said upper portion and said lower portion are statically held in said first locked extended position and such that said upper portion is prohibited from pivoting further away from said lower portion; and
a spacer, said spacer configured for placement between said upper and lower portions so that said ridge and said heel cup are statically held in relation to one another in a spacer-locked position in which said upper portion extends from said lower portion at an angle less than that of said first locked extended position and so that said upper portion is prohibited from pivoting further away from said lower portion and prohibited from pivoting nearer to said lower portion.

2. The device of claim 1 further comprising, a securing mechanism configured to secure said upper portion to a lower posterior portion of a leg and to secure said lower portion to a portion of a foot, said securing mechanism flexible in at least one area above said lower portion so as to allow for adjustable degrees of dorsiflexion while preventing plantar flexion past said inclined foot bed.

3. The device of claim 1 wherein said upper portion extends from said lower portion at an angle of less than 90° when said upper portion and said lower portions are fully extended.

4. The device for treating plantar facitis as described in claim 1, further comprising a removable wedge foot bed insert being shaped and sized to be received in said lower portion, said wedge configured to be inclined from a heel part of said lower portion to a toe part of said lower section thereby forming an inclined foot bed which prevents plantar flexion; wherein the removable wedge foot bed insert results in a foot bed which is at an angle of less than 90° in relation to the upper portion.

5. The device for treating plantar facitis as described in claim 4, wherein the lower portion is at an adjustable angle of less than 90° to the upper portion and the removable wedge foot bed insert results in a foot bed which is at an angle of less than 85° in relation to the upper portion.

6. The device for treating plantar facitis as described in claim 4, wherein the lower portion is at an adjustable angle of less than 90° with respect to the upper portion and the removable wedge foot bed insert results in a foot bed which is at an angle of less than 80° in relation to the upper portion.

7. The device for treating plantar facitis as described in claim 4, wherein the lower portion is at an adjustable angle of less than 90° in relation to the upper portion and the removable wedge foot bed insert results in a foot bed which may vary from a maximum angle of less than 90° to a minimum angle of 75° in relation to the upper portion.

8. The device for treating plantar facitis as described in claim 1 wherein said device is dimensioned to correspond with an incremental sizing standard which is utilized with any standard system of shoe sizes, such that, for a patient normally wearing child-sized shoes, said device is dimensioned to be of a pediatric size, and such that, for a patient normally wearing small-sized shoes, said device is dimensioned to be of a small size, and such that, for a patient normally wearing medium-sized shoes, said device is dimensioned to be of a medium size, and such that, for a patient normally wearing large-sized shoes, said device is dimensioned to be of a large size, and such that, for a patient normally wearing extra-large-sized shoes, said device is dimensioned to be of an extra-large size.

9. The orthosis of claim 1, wherein said spacer comprises a top notch and a bottom notch, said top notch configured for receiving therein a section of a lower edge of said upper portion, said bottom notch configured for receiving therein a section of an upper edge of said lower portion.

10. An ankle-foot orthosis comprising:
a foldable orthotic having an upper portion selectively pivotally connected to a lower portion the upper and lower portions each having a generally U-shaped cross-sectional configuration, said upper and lower portions configured to fold upon one another in a first position and to extend to a second position, said lower portion attached to and extending away from said upper portion said lower portion having a foot bed and a generally U-shaped cross-sectional configuration, said lower portion containing a heel cup portion, said upper portion defining a ridge, said ridge configured to interlock with said heel cup portion such that when said foldable orthotic is in said second position, said heel cup portion and said ridge are statically interlocked such that said upper portion and said lower portion are statically held in said second position and such that said upper portion is prohibited from pivoting further away from said lower portion;
at least one spacer configured for insertion between said upper and lower portions so that said ridge and said heel cup are statically held in relation to one another in a spacer-locked position in which said upper portion extends from said lower portion at an angle less than that of said second position and so that said upper portion is prohibited from pivoting further away from said lower portion and prohibited from pivoting nearer to said lower portion; and
a removable wedge foot bed insert configured for placement onto said foot bed of said lower portion, said removable wedge foot bed insert, when placed on said lower portion, presents an inclined foot bed in which the medial side of said inclined foot bed is lower than the lateral side of said inclined foot bed, and the cross-section of said inclined foot bed from one side to the other shows a top surface angle of between 0° and 15°.

11. The ankle-foot orthosis of claim 10 wherein the upper portion has a length that is proportionally less than the length of the lower portion.

12. The orthosis of claim 10, wherein each of said spacers comprises a top notch and a bottom notch, said top notch configured for receiving therein a section of a lower edge of said upper portion, said bottom notch configured for receiving therein a section of an upper edge of said lower portion.

13. An ankle-foot orthosis comprising:
a foldable shell, having an upper portion pivotally connected to a lower portion, both upper and lower portions having generally U-shaped cross-sections configured to extend at an angle of less than 90° from said upper portion when the upper and lower portions are fully extended in a first locked extended position, the lower portions also having a generally flat foot bed portion, said generally flat foot bed portion having a heel portion and a toe portion, said heel portion narrower than said toe portion and designed for close anatomical fit with a heel of a human patient, said upper portion configured for close and anatomically conforming shape with a lower posterior portion of a human leg, said upper portion also having a concavity which conforms to said human leg and maintains a human heel in a floated position from said flat foot bed, said upper portion extending along a length to a location below the thickest portion of the gastroc-soleus muscles of a patient, the lower portion being configured to receive a removable wedge foot bed insert, and said foldable shell being shaped to define an opening around a medial and a lateral prominence of a human ankle, said lower portion containing a heel cup portion, said upper portion defining a ridge, said ridge configured to interlock with said heel cup portion such that when said foldable shell is in said first locked extended position, said heel cup portion and said ridge are statically interlocked such that said upper portion and said lower portion are statically held in said first locked extended position and such that said upper portion is prohibited from pivoting further away from said lower portion;
at least one spacer configured for insertion between said upper and lower portions so that said ridge and said heel cup are statically held in relation to one another in a spacer-locked position in which said upper portion extends from said lower portion at an angle less than that of said first locked extended position and so that said upper portion is prohibited from pivoting further away from said lower portion and prohibited from pivoting nearer to said lower portion; and
a removable wedge foot bed insert, said insert shaped and sized to be received in said foot bed portion, said wedge being inclined from said heel portion of the foot bed to a toe portion of the foot bed thereby forming an inclined foot bed which prevents plantar flexion, said the removable wedge foot bed insert made of a semi-rigid material and having a cushioning top surface;
a soft jacket having a securing means attached, said soft jacket configured to cover said inside and outside surfaces of said upper and lower portions, and to connect with a securing means; and
a securing mechanism for securing said foldable shell to the lower posterior portion of the leg and foot, said securing mechanism being flexible in at least one area above said foot bed to allow for adjustable degrees of dorsiflexion while preventing plantar flexion past the inclined foot bed.

14. The orthosis of claim 13, wherein said lower portion is at an angle of less than 90° with respect to said upper portion when said upper portion is fully extended.

15. The orthosis of claim 14, wherein the addition of the removable wedge foot bed insert results in a foot bed surface which is positioned at an angle of 85° in relation to the upper portion.

16. The orthosis of claim 14, wherein the inclusion of the removable wedge foot bed insert results in a foot bed which is positioned at an angle of 80° in relation to the upper portion.

17. The orthosis of claim 14, wherein the addition of the removable wedge foot bed insert results in a foot bed which may vary from a maximum angle of less than 90° to a minimum angle of 75° in relation to the upper portion.

18. The orthosis of claim 13, wherein each of said spacers comprises a top notch and a bottom notch, said top notch configured for receiving therein a section of a lower edge of said upper portion, said bottom notch configured for receiving therein a section of an upper edge of said lower portion.

* * * * *